United States Patent
Zhu et al.

(10) Patent No.: US 10,617,692 B2
(45) Date of Patent: Apr. 14, 2020

(54) PYRROLOPYRIMIDINE COMPRISING CYCLOPENTYL SUBSTITUENT

(71) Applicants: CENTAURUS BIOPHARMA CO., LTD., Beijing (CN); CHIA TAI TIANQING PHARMACEUTICAL GROUP CO., LTD., Jiangsu Province (CN); LIANYUNGANG RUNZHONG PHARMACEUTICAL CO., LTD., Lianyungang, Jiangsu (CN)

(72) Inventors: Li Zhu, Beijing (CN); Yangjian Liu, Beijing (CN); Chuanyu Zhang, Beijing (CN); He Wang, Beijing (CN); Hong Luo, Beijing (CN); Yinghui Sun, Beijing (CN); Yongxin Han, Beijing (CN)

(73) Assignees: CENTAURUS BIOPHARMA CO., Beijing (CN); CHIA TAI TIANQING PHARMACEUTICAL GROUP CO., Jiangsu Province (CN); LIANYUNGANG RUNZHONG PHARMACEUTICAL CO., LTD., Lianyungang, Jiangsu (CN)

(*) Notice: Subject to any disclaimer, the term of this patent is extended or adjusted under 35 U.S.C. 154(b) by 0 days.

(21) Appl. No.: 16/310,221

(22) PCT Filed: Jun. 15, 2017

(86) PCT No.: PCT/CN2017/088424
§ 371 (c)(1),
(2) Date: Dec. 14, 2018

(87) PCT Pub. No.: WO2017/215628
PCT Pub. Date: Dec. 21, 2017

(65) Prior Publication Data
US 2019/0183899 A1 Jun. 20, 2019

(30) Foreign Application Priority Data
Jun. 16, 2016 (CN) .......................... 2016 1 0427950

(51) Int. Cl.
A61K 31/519 (2006.01)
A61P 35/00 (2006.01)
C07D 487/04 (2006.01)

(52) U.S. Cl.
CPC ............ *A61K 31/519* (2013.01); *A61P 35/00* (2018.01); *C07D 487/04* (2013.01)

(58) Field of Classification Search
CPC .......................... A61K 31/519; C07D 487/04
USPC ....................................... 514/265.1; 544/280
See application file for complete search history.

(56) References Cited

U.S. PATENT DOCUMENTS

| | | |
|---|---|---|
| 2007/0135461 A1 | 6/2007 | Rodgers et al. |
| 2008/0312258 A1 | 12/2008 | Rodgers et al. |
| 2011/0086810 A1 | 4/2011 | Rodgers et al. |

FOREIGN PATENT DOCUMENTS

| | | |
|---|---|---|
| CN | 101448826 A | 6/2009 |
| CN | 101815717 A | 8/2010 |
| CN | 102596960 A | 7/2012 |
| CN | 105777754 A | 7/2016 |
| WO | 9962908 A1 | 12/1999 |
| WO | 9965909 A1 | 12/1999 |
| WO | 200142246 A2 | 6/2001 |
| WO | 200472063 A1 | 8/2004 |
| WO | 2004099204 A1 | 11/2004 |
| WO | 2004099205 A2 | 11/2004 |
| WO | 2007070514 A1 | 6/2007 |

OTHER PUBLICATIONS

International Search Report dated Aug. 7, 2017, mailed Sep. 7, 2017.
English Translation of International Search Report dated Aug. 7, 2017, mailed Sep. 7, 2017.
Chen et al., "Janus Kinase Deregulation in Leukemia and Lymphoma", Immunity 36, Apr. 20, 2012, Elsevier Inc., pp. 529-541.

*Primary Examiner* — Jeffrey H Murray
(74) *Attorney, Agent, or Firm* — Norris McLaughlin, P.A.

(57) ABSTRACT

A pyrrolopyrimidine comprising a cyclopentyi substituent. The present invention specifically relates to a compound represented by formula. A and a stereoisomer and pharmaceutically acceptable salt thereof. The invention further relates to a method for manufacturing the pyrrolopyrimidine comprising the cyclopentyl substituent represented by formula A, a pharmaceutical composition, and an application of the compound in treating a disease induced by Janus kinase.

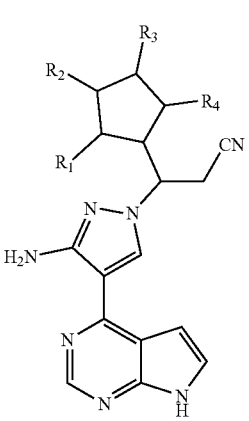

14 Claims, No Drawings

PYRROLOPYRIMIDINE COMPRISING CYCLOPENTYL SUBSTITUENT

CROSS-REFERENCE TO RELATED APPLICATIONS

This application is a 371 of PCT/CN2017/088424, filed Jun. 15, 2017, which claims foreign priority benefit under 35 U.S.C. § 119 of the Chinese Patent Application No. 201610427950.1 filed Jun. 16, 2016, the disclosures of which are incorporated herein by reference.

TECHNICAL FIELD

The present application belongs to the field of medical chemistry, and relates to a pyrrolopyrimidine compound having a substituted cyclopentyl group, a pharmaceutical composition containing the same, and a use thereof in the treatment of a disease mediated by Janus kinase.

BACKGROUND

Protein kinases (PKs), also called protein phosphokinases, are a sort of enzymes that catalyze the protein phosphorylation reaction. The protein kinases exert their physiological functions, including cell growth, survival and differentiation, organ formation and morphological change, neovascularization, tissue repair and regeneration, by catalyzing the phosphorylation of a protein. In addition to normal physiological functions, many protein kinases play an important role in human diseases (such as cancer). Cancerogenic protein kinases, i.e., a subgroup of protein kinases, when dysregulated, may cause tumor formation and growth, and further cause tumor metastasis and progression. To date, the cancerogenic protein kinases are one of the most important targets for treating cancers.

The protein kinases can be classified into receptor type and non-receptor type. A subfamily of the non-receptor type of tyrosine kinases (PTKs) comprises Janus kinase (JAK). As for the non-receptor type of tyrosine kinases, reference can be made in detail to, e.g., Bolen J B., Nonreceptor tyrosine protein kinases, Oncogene, 1993, 8(8): 2025-31.

Janus kinase (JAK) is a non-receptor type of tyrosine kinases (PTKs), which resides in cells and transduces cytokine stimulation signal via JAK-STAT pathway. By JAK-STAT pathway, a chemical signal outside the cell is transduced into a gene promoter on endonuclear DNA through cell membrane, and finally affects the DNA in cell to change its transcription and activity level. JAK-STAT pathway mainly consists of three components: (1) a receptor; (2) Janus kinase (JAK) and (3) a signal transducer and activator of transcription (STAT) protein. The receptor can be activated by interferon, interleukin, growth factor or other chemical messenger, and such activation leads to the phosphorylation of JAK itself. Then, the STAT protein bonds to the phosphorylated receptor, so that STAT is phosphorylated by JAK. After that, the phosphorylated STAT protein is isolated from the receptor, then dimerized and translocated into cell nucleus, thereby bonding to specific DNA site and changing transcription (Scott, M. J., C. J. Godshall et al. (2002). "Jaks, STATs, Cytokines, and Sepsis" Clin Diagn Lab Immunol 9(6): 1153-9).

JAK family plays a role in the cytokine-dependent regulation of proliferation and function of cells involved in immune response. At present, there are four known mammalian JAK family members: JAK1, JAK2, JAK3 and TYK2 (Tyrosine kinase 2). The JAK proteins have a size ranging from 120 kDa to 140 kDa, and comprise 7 conserved JAK homology (JH) domains. One of them is a functional catalytic kinase domain, and another is a pseudokinase domain which effectively exerts a regulatory function and/or acts as a docking site for STATs (Scott, Godshall et al. 2002, supra).

At present, the inhibitors for Janus kinase or relevant kinases have been reported, for example, in WO9965909, US20040198737, WO2004099204, WO2004099205, WO200142246, WO200472063, WO9962908, WO2007070514, etc.

SUMMARY OF THE INVENTION

In one aspect, the present application provides a compound represented by Formula A, a stereoisomer thereof, or a pharmaceutically acceptable salt thereof:

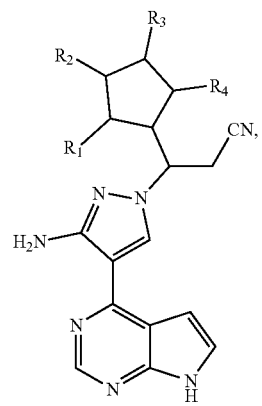

A wherein $R_1$ and $R_4$ are each independently selected from the group consisting of H, hydroxyl, and oxo; and $R_2$ and $R_3$ are each independently selected from the group consisting of H, and oxo; with the proviso that $R_1$, $R_2$, $R_3$, and $R_4$ are not all H.

In another aspect, the present application provides a pharmaceutical composition comprising a therapeutically effective amount of a compound represented by Formula A, a stereoisomer thereof, or a pharmaceutically acceptable salt thereof, and one or more pharmaceutically acceptable carriers or excipients.

In another aspect, the present application provides a compound represented by formula A, a stereoisomer thereof, or a pharmaceutically acceptable salt thereof, or a pharmaceutical composition described above, for use in the treatment of a disease mediated by Janus kinase.

In still another aspect, the present application provides the use of a compound represented by Formula A, a stereoisomer thereof, or a pharmaceutically acceptable salt thereof, or a pharmaceutical composition described above, in the preparation of a medicament for treating a disease mediated by Janus kinase.

In yet another aspect, the present application provides a method for treating a disease mediated by Janus kinase, comprising administering to a patient a therapeutically effective amount of a compound represented by Formula A, a stereoisomer thereof, or a pharmaceutically acceptable salt thereof, or a pharmaceutical composition described above.

DETAILED DESCRIPTION OF THE INVENTION

Definitions

The term "hydroxyl" refers to —OH group.

The term "oxo" refers to =O group.

The term "pharmaceutically acceptable" refers to those compounds, materials, compositions and/or dosage forms which are, within the scope of sound medical judgment, suitable for use in contact with the tissues of human beings and animals without excessive toxicity, irritation, allergic response, or other problems or complications, commensurate with a reasonable benefit/risk ratio.

A pharmaceutically acceptable salt can include, for example, a metal salt, an ammonium salt, a salt formed with an organic base, a salt formed with an inorganic acid, a salt formed with an organic acid, a salt formed with an alkaline or acidic amino acid, and the like. Non-limiting examples of a metal salt include, but not limited to, a salt of alkali metal, such as sodium salt, potassium salt, and the like; a salt of alkali earth metal, such as calcium salt, magnesium salt, barium salt, and the like; aluminum salt, and the like. Non-limiting examples of a salt formed with an organic base include, but not limited to, those salts formed with trimethylamine, triethylamine, pyridine, methylpyridine, 2,6-dimethylpyridine, ethanol amine, diethanol amine, triethanol amine, cyclohexylamine, dicyclohexylamine, and the like. Non-limiting examples of a salt formed with an inorganic acid include, but not limited to, those salts formed with hydrochloric acid, hydrobromic acid, nitric acid, sulfuric acid, phosphoric acid, and the like. Non-limiting examples of a salt formed with an organic acid include, but not limited to, those salts formed with formic acid, acetic acid, trifluoroacetic acid, fumaric acid, oxalic acid, malic acid, maleic acid, tartaric acid, citric acid, succinic acid, methanesulfonic acid, benzenesulfonic acid, p-methylbenzene sulfonic acid, and the like. Non-limiting examples of a salt formed with an alkaline amino acid include, but not limited to, those salts formed with arginine, lysine, ornithine, and the like. Non-limiting examples of a salt formed with an acidic amino acid include, but not limited to, those salts formed with aspartic acid, glutamic acid, and the like.

The pharmaceutically acceptable salt as used herein can be synthesized from a parent compound containing an acid radical or a base radical through a conventional chemical process. In general, the process for preparing such a salt comprises: reacting these compounds in the form of a free acid or base with stoichiometric appropriate base or acid in water or an organic solvent or a mixture of water and an organic solvent, and then separating a solid of salt product from the reaction solution. However, other processes for forming a salt can be used. In general, non-aqueous medium, such as ether, ethyl acetate, ethanol, isopropanol, acetonitrile and the like, is preferable.

Some of the compounds in the present application may exist as non-solvate form or solvate form, including hydrate form. In general, the solvate form is comparative to the non-solvate form, and both of them are contemplated by the present invention. Some of compounds in the present application may exist as polycrystalline or amorphous form.

Some of compounds in the present application may have unsymmetrical carbon atom (optical center) or double bond. Racemate, diastereoisomer, geometrical isomer and individual isomer are all included within the scope of the present invention.

The graphical representations for racemic, ambiscalemic and scalemic, or enantiomerically pure compounds herein are obtained from Maehr, J. Chem. Ed. 1985, 62: 114-120. Unless specified otherwise, the wedge shaped bond and dotted line bond are used to represent the absolute configuration of a stereoscopic center. Where the compounds herein contain an olefinic double bond or other geometrically unsymmetrical center, unless specified otherwise, they comprise E-, Z-geometrical isomers. Similarly, the tautomer forms are all included within the scope of the present invention.

The compounds of the present application may have particular geometrical isomers or stereoisomer forms. Such compounds are all contemplated in the present application, including cis- and trans-isomers, Z- and E-isomers, (−)- and (+)-enantiomers, (R)- and (S)-enantiomers, diastereoisomers, (D)-isomers, (L)-isomers, and racemic mixtures thereof and other mixtures, such as a enantiomer or diastereoisomer-rich mixture. All such mixtures are included within the scope of the present invention. Substituents such as alkyl group may have additional unsymmetrical carbon atoms. Such isomers and mixtures thereof are all included within the scope of the present invention.

Optically active (R)- and (S)-isomers and D- and L-isomers can be prepared by using chiral resolution, chiral synthesis or chiral reagents, or other conventional technology. If one enantiomer of certain compound of the present application is desired, this enantiomer can be prepared by an asymmetric synthesis or a derivatization process with a chiral adjuvant, which comprises separating a mixture of diastereoisomers, and cleaving assistant groups to provide a desired pure enantiomer. Alternatively, when the molecule contains an alkaline functional group (such as amino group) or an acidic functional group (such as carboxy group), a diastereoisomer salt can be formed by the molecule and an appropriate optically active acid or base, then the diastereoisomer is resolved by a fractional crystallization or chromatography as well-known in the art, thereby recovering a pure enantiomer. In addition, the separation of an enantiomer and a diastereoisomer is generally achieved by a chromatography using a chiral stationary phase, or optionally combining with a chemical derivatization process (e.g., using amine to produce a carbamate salt).

The compound of the present application can contain atomic isotopes at a non-natural ratio, on one or more atoms that constitute the compound. For example, the compound can be labeled with a radioactive isotope, such as tritium ($^3$H), iodine-125 ($^{125}$I) or carbon-14 ($^{14}$C). The transformations formed by all the isotopes for the compound of the present application, whether they are radioactive or not, are all contemplated by the present application The term "patient" refers to any animals including mammals, preferably mice, rats, other rodents, rabbits, dogs, cats, swine, cattle, sheep, horses, or primates, most preferably human being.

The phrase "therapeutically effective amount" as used herein refers to an amount of an active compound or pharmaceutical agent that elicits the biological or medical response that is being sought in a tissue, system, animal, subject or human being by a researcher, veterinarian, medical doctor or other clinicians, comprising one or more of:

(1) preventing a disease: for example, preventing a disease, disorder or condition in a subject who may be predisposed to the disease, disorder or condition but does not yet experience or display the pathology or symptomatology of the disease;

(2) inhibiting a disease: for example, inhibiting a disease, disorder or condition in a subject who is experiencing or displaying the pathology or symptomatology of the disease, disorder or condition (i.e., preventing the further development of the pathology and/or symptomatology);

(3) ameliorating a disease: for example, ameliorating a disease, disorder or condition in a subject who is experiencing or displaying the pathology or symptomatology of the disease, disorder or condition (i.e., reversing the pathology and/or symptomatology).

In one aspect, the present application provides a compound represented by formula A, a stereoisomer thereof, or a pharmaceutically acceptable salt thereof:

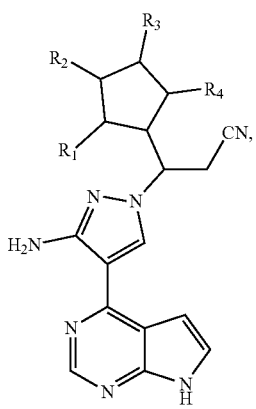

A wherein $R_1$ and $R_4$ are each independently selected from the group consisting of H, hydroxyl, and oxo; and $R_2$ and $R_3$ are each independently selected from the group consisting of H, and oxo; with the proviso that $R_1$, $R_2$, $R_3$, and $R_4$ are not all H.

Preferably, $R_1$ and $R_2$ are both H.

Preferably, one of $R_3$ and $R_4$ is H, and the other is hydroxyl or oxo.

In some embodiments of the present application, the compound represented by formula A is selected from compounds shown in Table 1 below:

TABLE 1

| No. | Name | Structure |
|---|---|---|
| Compound I | 3-[3-amino-4-(7H-pyrrolo [2,3-d]pyrimidin-4-yl)-1H-pyrazol-1-yl]-3-(3-hydroxyl-cyclopentyl)propionitrile | 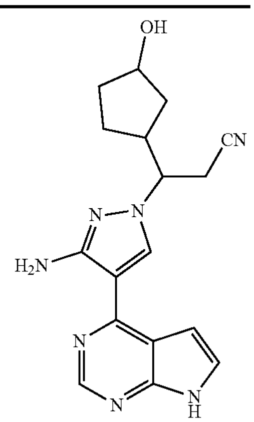 |

TABLE 1-continued

| No. | Name | Structure |
|---|---|---|
| Compound II | 3-[3-amino-4-(7H-pyrrolo [2,3-d]pyrimidin-4-yl)-1H-pyrazol-1-yl]-3-(2-hydroxyl-cyclopentyl)propionitrile | 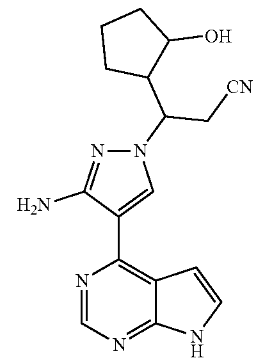 [SMILES: N#CCC(C1CCCC1O)n1cc(-c2ncnc3[nH]ccc23)c(N)n1] |
| Compound III | 3-[3-amino-4-(7H-pyrrolo [2,3-d]pyrimidin-4-yl)-1H-pyrazol-1-yl]-3-(3-oxocyclopentyl)propionitrile | 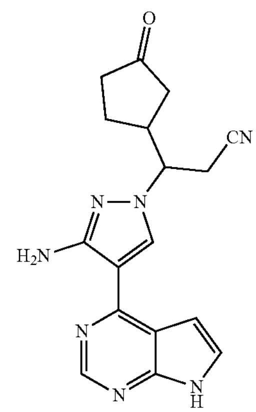 [SMILES: N#CCC(C1CCC(=O)C1)n1cc(-c2ncnc3[nH]ccc23)c(N)n1] |
| Compound IV | 3-[3-amino-4-(7H-pyrrolo [2,3-d]pyrimidin-4-yl)-1H-pyrazol-1-yl]-3-(2-oxocyclopentyl)propionitrile | 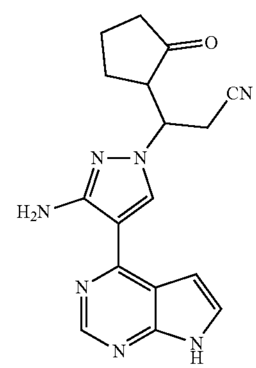 [SMILES: N#CCC(C1CCCC1=O)n1cc(-c2ncnc3[nH]ccc23)c(N)n1] |

In another aspect, the present application provides a pharmaceutical composition comprising a therapeutically effective amount of a compound represented by Formula A, a stereoisomer thereof, or a pharmaceutically acceptable salt thereof, and one or more pharmaceutically acceptable carriers or excipients.

In another aspect, the present application provides a compound represented by formula A, a stereoisomer thereof, or a pharmaceutically acceptable salt thereof, or a pharmaceutical composition described above, for use in the treatment of a disease mediated by Janus kinase.

In still another aspect, the present application provides the use of a compound represented by Formula A, a stereoisomer thereof, or a pharmaceutically acceptable salt thereof, or a pharmaceutical composition described above, in the preparation of a medicament for treating a disease mediated by Janus kinase.

In yet another aspect, the present application provides a method for treating a disease mediated by Janus kinase, comprising administering to a patient a therapeutically effective amount of a compound represented by Formula A, a stereoisomer thereof, or a pharmaceutically acceptable salt thereof, or a pharmaceutical composition described above.

The disease mediated by Janus kinase described in the present application includes, but not limited to, tumor (such as lymphoma, leukemia). Lymphoma described in the present application may include, but not limited to, Hodgkins disease or Non-Hodgkins lymphoma, and the Non-Hodgkins lymphoma includes, but not limited to, B-cell lymphoma and T-cell lymphoma. Leukemia described in the present application includes, but not limited to, acute lymphoblastic leukemia, chronic lymphocytic leukemia, acute myeloid leukemia, and chronic myelocytic leukemia.

The compounds in the examples of the present application exhibit significant JAK (such as JAK1, JAK2, JAK3, or TYK2) inhibitory activity. For example, in one or more tests herein, the compounds exhibit a JAK inhibitory activity of less than 1000 nM, preferably a JAK inhibitory activity of less than 200 nM, more preferably a JAK inhibitory activity of less than 100 nM, and particularly preferably a JAK inhibitory activity of less 30 nM.

The compounds in the examples of the present application are preferably JAK2-selective inhibitors. That is, the selectivity of the compounds for JAK2 is higher than the selectivity for JAK1, JAK3, and TYK2. The selectivity for JAK2 can be at least 1-fold, 2-fold, 5-fold, 10-fold, 20-fold, 50-fold or more the selectivity for JAK1, JAK3, and TYK2.

Compared with other JAK inhibitors, some representative compounds of the present application also exhibit especially excellent pharmacokinetic properties, and these compounds, as active ingredients, can be administered to a patient at a lower dose, thereby reducing the therapy cost of the patient.

When used as a medicine, the compounds of the present application can be administered in the form of pharmaceutical compositions. These compositions can be prepared in a manner well-known in the pharmaceutical art, and can be administered by a variety of routes, depending upon whether a local or systemic treatment is desired and upon the area to be treated. Administration may be topical (for example, transdermal, epidermal, ophthalmic and mucous membranes including intranasal, vaginal and rectal delivery), pulmonary (for example, by inhalation or insufflation of powders or aerosols, including by nebulizer; intratracheal or intranasal), oral or parenteral. Parenteral administration includes intravenous, intraarterial, subcutaneous, intraperitoneal, or intramuscular injection or infusion; or intracranial such as intrathecal or intraventricular administration. Parenteral administration may be in the form of a single large dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, water, powders or oily bases, thickeners and the like may be necessary or desirable. Coated condoms, gloves and the like may also be useful.

The present application also includes a pharmaceutical composition which contains one or more of the compounds of the present application above as active ingredient in combination with one or more pharmaceutically acceptable carriers. During the preparation of the composition of the present application, the active ingredient is typically mixed with an excipient, diluted by an excipient or enclosed within such a carrier in the form of, for example, a capsule, sachet, paper or other container. When the excipient serves as a diluent, it can be a solid, semi-solid, or liquid material, which acts as a vehicle, carrier or medium for an active ingredient. Therefore, the composition can be in the form of tablets, pills, powders, lozenges, sachets, cachets, elixirs, suspensions, emulsions, solutions, syrups, aerosols (a solid or dissolved in a liquid medium); ointments containing, for example, up to 10% by weight of an active compound, soft and hard gelatin capsules, suppositories, sterile injectable solutions, and sterile packaged powders.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying agents and suspending agents; preserving agents such as methylbenzoate and hydroxyl propyl benzoate; sweetening agents; and flavoring agents. The compositions of the present application can be formulated by employing procedures known in the art, so as to provide quick, sustained or delayed release of the active ingredient after administration to the patient.

The compositions may be formulated in a unit dosage form, each dosage containing from about 5~1000 mg, more typically about 100~500 mg, of the active ingredient. The term "unit dosage form" refers to physically discrete unit suitable as unitary dosage for human patient and other mammals, each unit containing a predetermined quantity of the active material calculated to be able to produce the desired therapeutic effect, and mixed with a suitable pharmaceutical excipient.

The active compound can be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

For preparing a solid composition such as tablets, the principal active ingredient is mixed with a pharmaceutical excipient to form a solid preformulation composition containing a homogeneous mixture of a compound of the present application. When these preformulation compositions are referred to be homogeneous, it means that the active ingredient is typically dispersed evenly throughout the composition so that the composition can be readily subdivided into equally effective unit dosage forms such as tablets, pills and capsules. This solid preformulation is then subdivided into unit dosage forms of the types described above containing, for example, about 0.1~1000 mg of the active ingredient of the present application.

The tablets or pills of the present application can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intactly through the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms for administration orally or by injection, in which the compounds and compositions of the present application can be incorporated, include aqueous solutions, suitably flavored syrups, aqueous or oil suspensions, and emulsions flavored with edible oils such as cottonseed oil, sesame oil, coconut oil, or peanut oil, as well as elixirs and similar pharmaceutical vehicles.

Compositions for inhalation or insufflation include solutions and suspensions dissolved in pharmaceutically acceptable aqueous or organic solvents, or mixtures thereof, and powders. The liquid or solid composition may contain a suitable pharmaceutically acceptable excipient as described above. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face masks tent, or intermittent positive pressure breathing machine. Solution, suspension, or powder compositions can be administered orally or nasally from devices which deliver the formulation in an appropriate manner.

The amount of the compound or composition administered to a patient will vary depending upon what is being administered, the purpose of the administration, such as prophylaxis or therapy, the state of the patient, the manner of administration, and the like. In therapeutic application, the composition can be administered to a patient already suffering from a disease in an amount sufficient to cure or at least partially arrest the symptom of the disease and its complication. Effective dose will depend on the disease condition being treated as well as the judgment of the attending clinician depending upon factors such as the severity of the disease, the age, weight and general condition of the patient, and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being mixed with a sterile aqueous carrier prior to administration. The pH of the compound preparations typically will be 3~11, more preferably 5~9 and most preferably 7~8. It will be understood that use of certain of the foregoing excipients, carriers, or stabilizers will result in the formation of pharmaceutical salts.

The therapeutic dosage of the compounds of the present application can be determined according to, for example, the particular use for which the treatment is made, the manner of administration of the compound, the health and condition of the patient, and the judgment of the prescribing physician. The proportion or concentration of a compound of the present application in a pharmaceutical composition can vary depending upon a number of factors including dosage, chemical characteristics (e.g., hydrophobicity), and the route of administration. For example, the compound of the present application can be provided in an aqueous physiological buffer solution containing about 0.1~10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and progression extent of the disease or condition, the overall healthy status of the particular patient, the relative biological efficacy of the compound selected, formulation of the excipient, and its route of administration. Effective doses can be obtained by extrapolating from dose-response curves derived from in vitro or animal model test systems.

The compounds of the present application can be prepared by various synthesis processes well-known to a person skilled in the art, including the specific embodiments illustrated in the following description, the embodiments obtained by combining the specific embodiments with other chemical synthesis processes, as well as equivalent embodiments well-known to the skilled person in the art. The preferable embodiments include, but not limited to, the Examples of the present application.

The chemical reactions in the specific embodiments of the present application are carried out in appropriate solvents that must be suitable for chemical modification of the present invention, as well as the reagents and materials needed in such modification. In order to obtain the compounds of the present invention, a person skilled in the art sometimes need to modify or select synthesis steps or reaction processes on the basis of the existing embodiments.

It is one important consideration factor for any synthesis scheme in the art to select appropriate protecting groups for the reactive functional groups (such as the amino group in the present invention). As for any trained practitioner, Greene and Wuts, Protective Groups In Organic Synthesis, Wiley and Sons, 1991, is authoritative in this aspect. All references cited in the present invention are incorporated herein by reference in their entirety.

The reactions herein can be monitored according to any known suitable methods in the art. For example, the formation of a product can be monitored by broad spectrum methods, for example, nuclear magnetic resonance spectroscopy (such as $^1H$ or $^{13}C$), infrared spectroscopy, spectrophotometry (such as UV-visible light) or mass spectrography, or by chromatography, for example, high performance liquid chromatography (HPLC) or thin layer chromatography.

The compounds of the present application can be prepared by many preparation pathways known in literatures. An example of synthetic methods for preparing the compounds of the present application is provided in following schemes.

As shown in Scheme 1, the synthesis of the compound I starts from 3-oxocyclopentanecarboxylic acid 1. 3-Oxocyclopentanecarboxylic acid 1 is reduced to obtain alcohol 2, which is esterified to obtain ethyl ester 3, and a hydroxy group is protected to obtain ester 4. Ester 4 is reduced with a reductant such as DIBAL-H to obtain aldehyde 5, which then reacts with the compound 6 to obtain the compound 7 through H-W-E reaction (Horner-Wadsworth-Emmons reaction). Compound 7 then reacts with pyrazole 8 in the presence of a base such as DBU to obtain the compound 9 through a Michael addition reaction, and then a TBS protective group and a SEM protective group of the compound 9 are removed to obtain the compound I under an acidic condition.

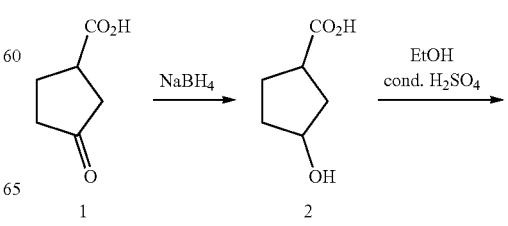

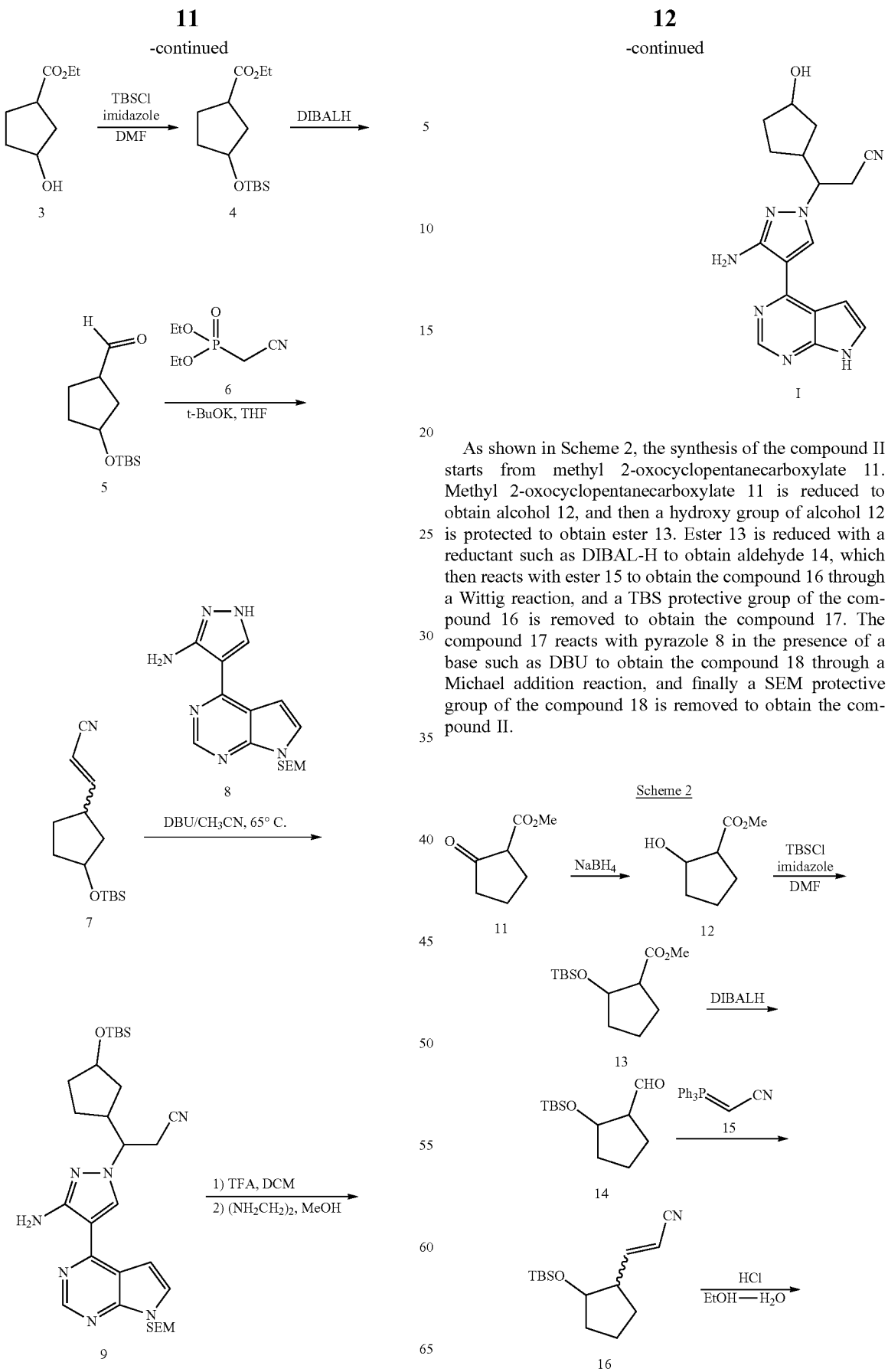

As shown in Scheme 2, the synthesis of the compound II starts from methyl 2-oxocyclopentanecarboxylate 11. Methyl 2-oxocyclopentanecarboxylate 11 is reduced to obtain alcohol 12, and then a hydroxy group of alcohol 12 is protected to obtain ester 13. Ester 13 is reduced with a reductant such as DIBAL-H to obtain aldehyde 14, which then reacts with ester 15 to obtain the compound 16 through a Wittig reaction, and a TBS protective group of the compound 16 is removed to obtain the compound 17. The compound 17 reacts with pyrazole 8 in the presence of a base such as DBU to obtain the compound 18 through a Michael addition reaction, and finally a SEM protective group of the compound 18 is removed to obtain the compound II.

Scheme 3

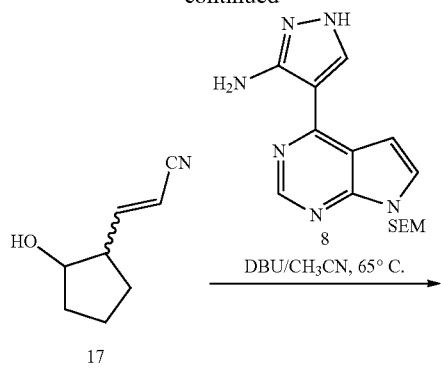

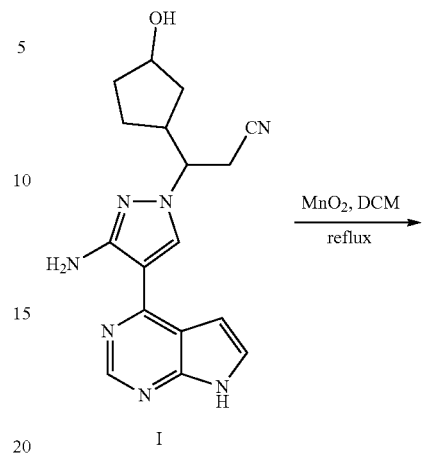

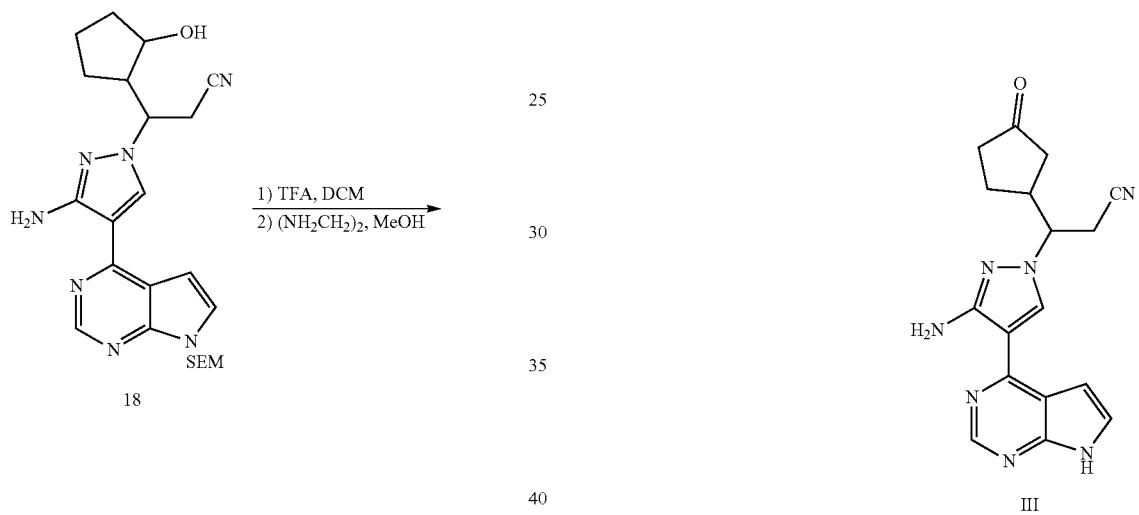

Synthesis of the compound III is shown in Scheme 3, in which the compound I is oxidized in the presence of manganese dioxide to obtain the compound III.

Synthesis of the compound IV is shown in scheme 4, in which the compound 18 is oxidized in the presence of manganese dioxide to obtain the compound 19, and then the SEM of the compound 19 is removed to obtain the compound IV.

Scheme 4

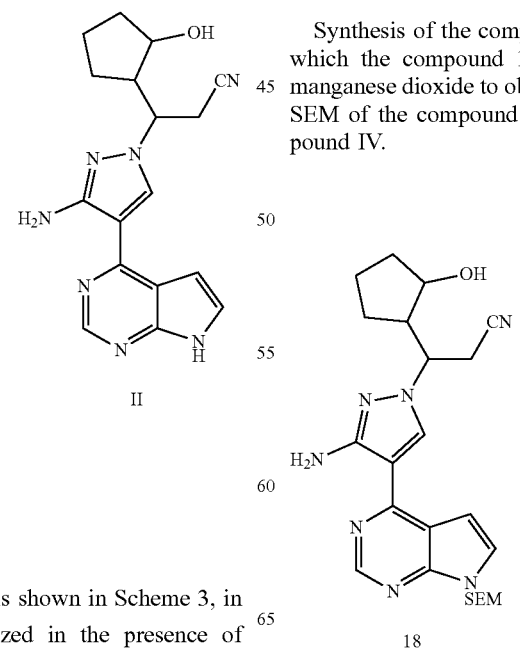

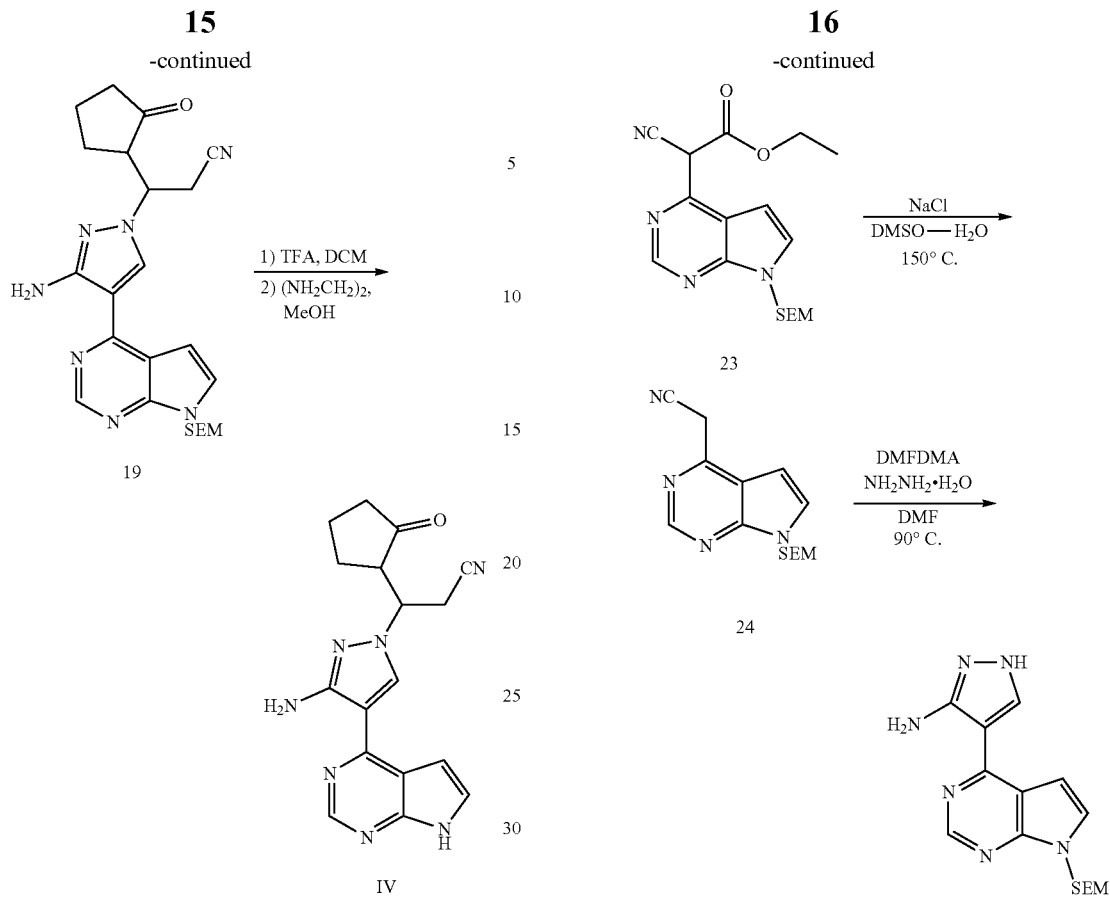

Synthesis of the intermediate aminopyrazole 8 is shown in Procedure 1. Pyrrolo[2,3-b]pyrimidine 20 as a starting material is protected by an appropriate protective group such as SEM to obtain the compound 21. The compound 21 reacts with ethyl cyanoacetate 22 to obtain the compound 23, which is then decarboxylated to obtain the compound 24. Then the compound 24 reacts with N,N-dimethylformamide dimethyl acetal (DMF-DMA) and hydrazine hydrate to obtain aminopyrazole 8 through a one-pot reaction.

Procedure 1

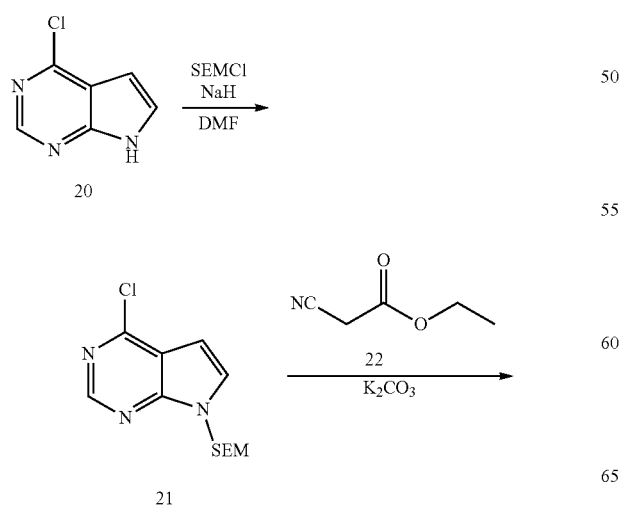

EXAMPLES

The present invention will be described in more detail by way of specific examples. The following examples are provided for illustrative proposes, and are not intended to limit the present invention in any manner. A person skilled in the art will readily recognize that a variety of non-critical parameters may be changed or modified to obtain substantively the same results.

The compounds in the following examples are found to be JAK inhibitors according to one or more tests herein.

Preparation of intermediate 8

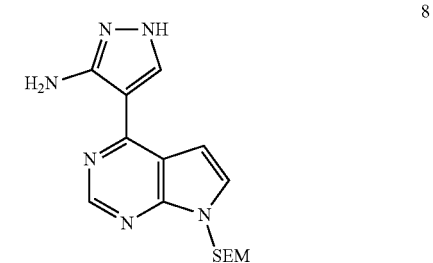 [SMILES: C[Si](C)(C)CCOCn1ccc2c(-c3c[nH]nc3N)ncnc21]

Step A: 4-chloro-7-{[2-(trimethylsilyl)ethoxy]methyl}-7H-pyrrolo[2,3-d]pyrimidine

To a solution of 4-chloro-7H-pyrrolo[2,3-d]pyrimidine (20.0 g, 130.4 mmol, 1.0 eq.) in dry DMF was added NaH (6.6 g, 57% content, 156.8 mmol, 1.2 eq.), under stirring in an ice bath. After the reactants were stirred for 1 hr at room temperature, SEMCl (26.1 g, 156.5 mmol, 1.2 eq.) was added dropwise under the cooling of an ice bath. After completion of the addition, the reactants were stirred for 1 hr in an ice bath, then the reaction was quenched by adding water, and the resulting mixture was extracted with ethyl acetate. The combined organic phase was washed with brine, dried over sodium sulfate, filtered and concentrated in vacuo. The resulting residue was separated by column chromatography on silica gel column to give 4-chloro-7-{[2-(trimethylsilyl)ethoxy]methyl}-7H-pyrrolo[2,3-d]pyrimidine (33.4 g, 90% yield).

$^1$HNMR (400 MHz, CDCl$_3$-d$_3$) δ8.67 (s, 1H), 7.39 (d, J=3.6 Hz, 1H), 6.67 (d, J=3.6 Hz, 1H), 5.65 (s, 2H), 3.53 (dd, J=9.2 Hz, J=8.0 Hz, 2H), 0.91 (t, J=8.4 Hz, 2H), 0.00 (s, 9H). m/z=284[M+1]+.

Step B: ethyl 2-cyano-2-(7-{[2-(trimethylsilyl)ethoxy]methyl}-7H-pyrrolo[2,3-d]pyrimidin-4-yl)acetate

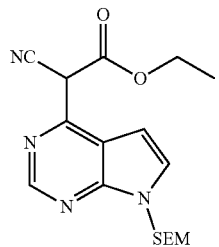 [SMILES: CCOC(=O)C(C#N)c1ncnc2c1ccn2COCC[Si](C)(C)C]

To a mixture of ethyl cyanoacetate (40.1 g, 354.0 mmol, 3.0 eq.) and potassium carbonate (33.0 g, 238 mmol, 2.0 eq.) was added 4-chloro-7-{[2-(trimethylsilyl)ethoxy]methyl}-7H-pyrrolo[2,3-d]pyrimidine (33.5 g, 118 mmol, 1.0 eq.) under stirring at room temperature. The reactants were warmed to 60° C. and reacted for 0.5 hr, then warmed to 130° C. and reacted for 1.0 hr. After the resulting mixture was cooled to room temperature, the reaction was quenched by adding water, and the resulting mixture was extracted with ethyl acetate. The combined organic phase was washed with brine, dried over sodium sulfate, filtered and concentrated in vacuo. The resulting residue was separated by column chromatography on silica gel column to give ethyl 2-cyano-2-(7-{[2-(trimethylsilyl)ethoxy]methyl}-7H-pyrrolo[2,3-d]pyrimidin-4-yl)acetate (30.6 g, 72% yield).

$^1$HNMR (400 MHz, CDCl$_3$-d$_3$): δ13.87 (brs, 1H), 8.05 (s, 1H), 7.44 (d, J=4.0 Hz, 1H), 7.20 (d, J=3.6 Hz, 1H), 5.57 (s, 2H), 4.30 (dd, J=14.4 Hz, J=7.2 Hz, 2H), 3.5 (t, J=8.4 Hz, 2H), 1.37 (t, J=7.2 Hz, 3H), 0.92 (t, J=8.4 Hz, 2H), 0.00 (s, 9H). m/z=361[M+1]+.

Step C: 2-(7-{[2-(trimethylsilyl)ethoxy]methyl}-7H-pyrrolo[2,3-d]pyrimidin-4-yl) acetonitrile

To ethyl 2-cyano-2-(7-{[2-(trimethylsilyl)ethoxy]methyl}-7H-pyrrolo[2,3-d]pyrimidin-4-yl)acetate (30.6 g, 84.9 mmol, 1.0 eq.) in a mixed solvent of DMSO and water was added sodium chloride (49.7 g, 849.0 mmol, 10.0 eq.) under stirring at room temperature. The reaction liquid was protected with nitrogen gas to react for 5 days at 150° C. After the reaction liquid was cooled to room temperature, the reaction was quenched by adding water, and the resulting mixture was extracted with ethyl acetate. The combined organic phase was washed with brine, dried over sodium sulfate, filtered and concentrated in vacuo. The resulting residue was separated by column chromatography on silica gel column to give 2-(7-{[2-(trimethyl silyl)ethoxy]methyl}-7H-pyrrolo[2,3-d]pyrimidin-4-yl)acetonitrile (18.4 g, 75% yield).

$^1$HNMR (400 MHz, CDCl$^3$-d$_3$) δ8.87 (s, 1H), 7.40 (d, J=3.6 Hz, 1H), 6.80 (d, J=3.6 Hz, 1H), 5.67 (s, 2H), 4.15 (s, 2H), 3.53 (t, J=8.4 Hz, 2H), 0.92 (t, 8.4 Hz, 2H), 0.01 (s, 9H). m/z=289[M+1]+.

Step D: 4-(7-{[2-(trimethyl silyl)ethoxy]methyl}-7H-pyrrolo[2,3-d]pyrimidin-4-yl)-3-amino-1H-pyrazole

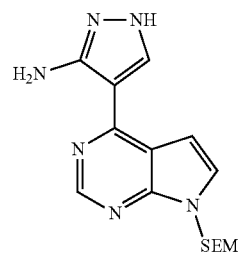 [SMILES: C[Si](C)(C)CCOCn1ccc2c(-c3c[nH]nc3N)ncnc21]

To a solution of 2-(7-{[2-(trimethylsilyl)ethoxy]methyl}-7H-pyrrolo[2,3-d]pyrimidin-4-yl)acetonitrile (830 g, 2.88 mol, 1.0 eq.) and DMF-DMA (1029 g, 8.64 mol, 3 eq.) in DMF (2.5 L) was added hydrazine hydrate (85%, 1802 g, 28.8 mol, 10.0 eq.) under stirring at room temperature. The reaction solution was stirred and refluxed for 3 hours under the protection of nitrogen gas at 90° C. The reaction solution was cooled to room temperature, and then 1 L of water was added thereto, stirred, filtered under suction, and dried to afford 4-(7-{[2-(trimethylsilyl)ethoxy]methyl}-7H-pyrrolo[2,3-d]pyrimidin-4-yl)-3-amino-1H pyrazole (365 g, 39% yield).

¹HNMR (400 MHz, DMSO-d₆) δ12.20 (brs, 1H), 8.75 (s, 1H), 8.30 (brs, 1H), 7.71 (d, J=3.2 Hz, 1H), 7.11 (d, J=3.6 Hz, 1H), 6.66 (brs, 2H), 5.70 (s, 2H), 3.62 (t, J=8.0 Hz, 2H), 0.93 (t, J=8.0 Hz, 2H), 0.00 (s, 9H). m/z=331[M+1]⁺.

Example 1 3-[3-amino-4-(7H-pyrrolo[2,3-d]pyrimidin-4-yl)-1H-pyrazol-1-yl]-3-(3-hydroxylcyclopentyl)propionitrile

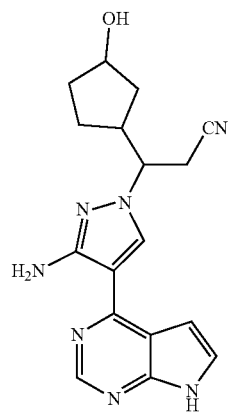 [SMILES: N#CCC(C1CCC(O)C1)n1cc(-c2ncnc3[nH]ccc23)c(N)n1]

Step A: 3-hydroxylcyclopentanecarboxylic acid

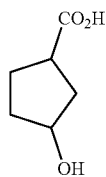

To a solution of 3-carbonylcyclopentanecarboxylic acid (3.7 g, 28.9 mmol) in methanol was added sodium borohydride (1.64 g, 43.2 mmol) in portions in an ice bath. After completion of the addition, the reaction mixture was stirred at room temperature. After completion of the reaction, 1M hydrochloric acid solution was added to the reaction liquid to quench the reaction. The solvent was removed to give a crude product which was directly used in a next step.

Step B: ethyl 3-hydroxylcyclopentanecarboxylate

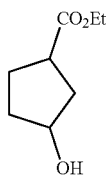

To a solution of the crude product obtained from the step A in ethanol was added concentrated sulfuric acid (1.5 mL), and the mixture was reacted overnight at 90° C. After completion of the reaction, the reaction was quenched by adding saturated sodium bicarbonate solution, and ethanol was removed. Water was added to the concentrate, and the resulting mixture was extracted with ethyl acetate, and separated by column chromatography (ethyl acetate/petroleum ether=1/5) to give racemic ethyl 3-hydroxylcyclopentanecarboxylate (2.27 g, 50% yield).

¹HNMR (400 MHz, CDCl₃-d₃) δ4.30-4.34 (m, 1H), 4.10-4.18 (m, 2H), 2.82-2.90 (m, 1H), 1.60-2.20 (m, 7H), 1.20-1.29 (m, 3H).

Step C: ethyl 3-tert-butyldimethylsiloxycyclopentanecarboxylate

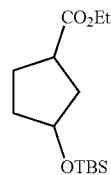

To a solution of 1H-imidazole (1.96 g, 28.73 mmol) and tert-butyldimethylsilyl chloride (2.17 g, 14.37 mmol) in DMF was added ethyl 3-hydroxylcyclopentanecarboxylate (2.27 g, 14.37 mmol). The mixture was stirred overnight until the reaction of starting materials was completed. The reaction liquid was extracted with n-hexane and the extractant was washed with water three times, and dried over sodium sulfate. The solvent was removed to give racemic ethyl 3-tert-butyldimethylsiloxycyclopentanecarboxylate (3.92 g, 100%).

¹HNMR (400 MHz, CDCl₃-d₃) δ4.10-4.19 (m, 1H), 4.05-4.09 (m, 2H), 2.64-2.68 (m, 1H), 2.00-2.07 (m, 2H), 1.62-1.86 (m, 4H), 1.19-1.23 (m, 3H), 0.82-0.87 (m, 9H), −0.02-0.06 (m, 6H).

Step D: 3-tert-butyldimethylsiloxycyclopentanecarbaldehyde

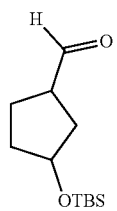

To a solution of racemic ethyl 3-tert-butyldimethylsiloxycyclopentanecarboxylate (3.92 g) in n-hexane was added a 1.2M solution of diisobutylaluminum hydride in toluene dropwise at −78° C., and then reacted for 1 hr. After completion of the reaction, the reaction was quenched by adding methanol. The mixture was washed with a saturated sodium bicarbonate solution, dried over sodium sulfate, and separated by column chromatography (ethyl acetate/petroleum ether=1:30) to give the title product (2.34 g, 65% yield).

¹HNMR (400 MHz, CDCl₃-d₃) δ9.64 (s, 1H), 4.29-4.31 (m, 1H), 2.64-2.68 (m, 1H), 1.56-2.13 (m, 6H), 0.82-0.87 (m, 9H), 0.00-0.15 (m, 6H).

Step E: 3-[3-(tert-butyldimethylsiloxy)cyclopentyl] acrylonitrile

To a solution of potassium tert-butoxide (246.8 mg, 2.2 mmol) in tetrahydrofuran was added diethyl cyanomethyl phosphate (426.0 mg, 2.4 mmol) in an ice bath. The ice bath was removed, and the solution was stirred for 15 min at room temperature, and then cooled to 0° C. again. 3-Tert-butyldimethylsiloxycyclopentanecarbaldehyde (458.0 mg, 2.0 mmol) was added dropwise to the solution. The resulting solution was reacted for 1 hr at room temperature until the reaction was completed, and then separated by column chromatography (ethyl acetate/petroleum ether=1/60) to give the title product (435 mg, 87% yield).

$^1$HNMR (400 MHz, CDCl$_3$-d$_3$) δ6.50-6.80 (m, 1H), 5.16-5.29 (m, 1H), 4.27-4.33 (m, 1H), 2.64-2.68 (m, 1H), 1.40-2.13 (m, 6H), 0.85-0.89 (m, 9H), 0.00-0.07 (m, 6H).

Step F: 3-[3-amino-4-(7-{[2-(trimethylsilyl)ethoxy]methyl}-7H-pyrrolo[2,3-d]pyrimidin-4-yl)-1H-pyrazol-1-yl]-3-[3-(t-butyldimethylsiloxy)-cyclopentyl]propionitrile

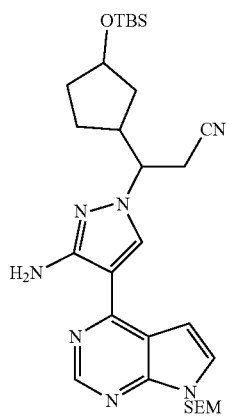 [SMILES: CC(C)(C)[Si](C)(C)OC1CCC(C(CC#N)n2cc(-c3ncnc4c3ccn4COCC[Si](C)(C)C)c(N)n2)C1]

3-[3-(t-butyldimethylsiloxy)cyclopentyl]acrylonitrile (0.8 g, 3.0 mmol), 4-(7-{[2-(trimethyl silyl)ethoxy]methyl}-7H-pyrrolo[2,3-d]pyrimidin-4-yl)-3-amino-1H-pyrazole (1.0 g, 3.0 mmol), and DBU (0.9 g, 6.0 mmol) were dissolved in 10 mL of acetonitrile, and stirred overnight at 65° C. (for about 15 hours). After the reaction was cooled to room temperature, 20 mL of water was added thereto, and extracted with ethyl acetate (50 mL×3). The organic phase was combined, washed with a saturated sodium chloride solution (100 mL×2), and then dried over anhydrous sodium sulfate. The organic solvent was removed by distillation under reduced pressure, and the residue was separated by silica gel column chromatography (a mixed solvent of dichloromethane:methanol=30:1 as an eluent) to afford 3-[3-amino-4-(7-{[2-(trimethylsilyl)ethoxy]methyl}-7H-pyrrolo[2,3-d]pyrimidin-4-yl)-1H-pyrazol-1-yl]-3-[3-(t-butyldimethylsiloxy)-cyclopentyl]propionitrile as a diastereoisomeric mixture (530 mg, 30% yield).

$^1$H NMR (400 MHz, CDCl$_3$-d$_3$) δ8.82 (1H, s), 8.03 (0.2H, s), 8.02 (0.2H, s), 8.01 (0.3H, s), 8.00 (0.3H, s), 7.37-7.38 (1H, m), 6.68-6.71 (1H, m), 5.66-5.71 (4H, m), 4.26-4.40 (1H, m), 3.99-4.23 (1H, m), 3.56 (2H, t, J=8.4 Hz), 3.05-3.14 (1H, m), 2.86-2.95 (1.4H, m), 2.56-2.71 (0.6H, m), 1.40-2.16 (5H, m), 0.94 (2.7H, s), 0.90 (2.7H, s), 0.90 (1.8H, s), 0.87 (1.8H, s), 0.06 (2H, t, J=5.6 Hz), −0.03 (6H, s), −0.06 (9H, s). m/z=582[M+1]$^+$.

Step G: 3-[3-amino-4-(7H-pyrrolo[2,3-d]pyrimidin-4-yl)-1H-pyrazol-1-yl]-3-(3-hydroxylcyclopentyl)propionitrile

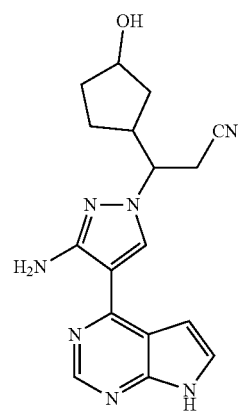 [SMILES: N#CCC(C1CCC(O)C1)n1cc(-c2ncnc3[nH]ccc23)c(N)n1]

To a solution of 3-[3-amino-4-(7-{[2-(trimethylsilyl)ethoxy]methyl}-7H-pyrrolo[2,3-d]pyrimidin-4-yl)-1H-pyrazol-1-yl]-3-(2-hydroxylcyclopentyl)propionitrile (500 mg, 0.86 mmol) in dichloromethane (50 mL) was added trifluoroacetic acid (5 mL) under stirring in an ice bath. The reaction solution was stirred overnight under the protection of nitrogen gas at room temperature, and then concentrated in vacuo. The residue was dissolved in dichloromethane, and concentrated in vacuo twice. The concentrate was dissolved in methanol (50 mL), and ethylenediamine (5 mL) was added. The resulting solution was stirred for 1 hour at room temperature, and concentrated in vacuo. The resulting concentrate was diluted with water and ethyl acetate, and extracted with ethyl acetate. The combined organic phase was washed with a brine solution, dried over sodium sulfate, filtered, and concentrated in vacuo. The resulting concentrate was separated by silica gel column chromatography (dichloromethane:methanol=20:1) to afford 3-[3-amino-4-(7H-pyrrolo[2,3-d]pyrimidin-4-yl)-1H-pyrazol-1-yl]-3-(3-hydroxyl-cyclopentyl)propionitrile (200 mg, 69% yield).

$^1$H NMR (400 MHz, CDCl$_3$-d$_3$) δ9.38-9.46 (1H, brs), 8.79 (0.4H, s), 8.78 (0.6H, s), 8.02-8.05 (1H, m), 7.29-7.32 (1H, m), 6.64-6.67 (1H, m), 5.70 (1.2H, s), 5.68 (0.8H, s), 4.34-4.48 (1H, m), 4.18-4.25 (0.6H, m), 4.02-4.07 (0.4H, m), 3.05-3.14 (1H, m), 2.79-2.97 (1.4H, m), 2.55-2.72 (0.6H, m), 1.52-2.22 (7H, m). m/z=338[M+1]$^+$.

Example 2 3-[3-amino-4-(7H-pyrrolo[2,3-d]pyrimidin-4-yl)-1H-pyrazol-1-yl]-3-(2-hydroxyl-cyclopentyl)propionitrile

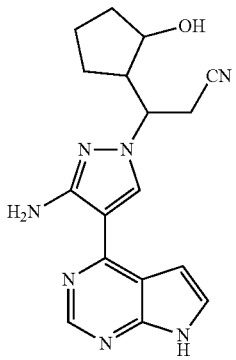 [SMILES: N#CCC(C1CCCC1O)n1cc(-c2ncnc3[nH]ccc23)c(N)n1]

Step A: methyl 2-hydroxylcyclopentanecarboxylate

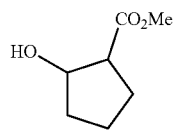

Methyl 2-oxocyclopentanecarboxylate (35.0 g, 246.2 mmol) was dissolved in anhydrous methanol (300 mL), and cooled to −20° C. in a liquid nitrogen-ethanol bath. Sodium borohydride (10.2 g, 270.1 mmol) was added in portions. After completion of the addition, the resulting solution was continuously reacted for 30 minutes at −20° C., then quenched by adding 600 mL of water, and adjusted to pH 4 with a saturated aqueous solution of citric acid, and then the resulting product was extracted with ethyl acetate twice (500 mL/time). The organic phase was combined, washed with a saturated aqueous solution of sodium chloride twice (500 mL/time), and dried over 100 g of anhydrous sodium sulfate. The solvent was removed by distillation under reduced pressure to afford methyl 2-hydroxylcyclopentanecarboxylate as light yellow oil (22.4 g, 63.2% yield).

$^1$H NMR (400 MHz, CDCl$_3$-d$_3$) δ4.36-4.46 (1H, m), 3.73 (1.8H, s), 3.71 (1.2H, s), 3.00 (0.6H, d, J=2.8 Hz), 2.64-2.72 (1H, m), 2.14 (0.4H, d, J=3.6 Hz), 1.87-2.15 (3H, m), 1.76-1.82 (2H, m), 1.59-1.71 (1H, m).

Step B: Methyl 2-t-butyldimethylsiloxycyclopentanecarboxylate

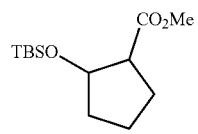

To a solution of 1H-imidazole (23.2 g, 342 mmol) and t-butyldimethylsilyl chloride (25.7 g, 171 mmol) in DMF (600 mL) was added methyl 2-t-butyldimethylsiloxycyclopentanecarboxylate (22.4 g, 155 mmol). The resulting mixture was stirred overnight. After complete consumption of the starting materials, 1.2 L of water was added, and the reaction solution was extracted with ethyl acetate (500 mL×3). The organic phase was washed with a saturated aqueous solution of sodium chloride (500 mL×2), and dried over anhydrous sodium sulfate. The solvent was removed to afford racemic methyl 2-t-butyldimethylsiloxycyclopentanecarboxylate as light yellow oily liquid (36.1 g, 90%).

$^1$H NMR (400 MHz, CDCl$_3$-d$_3$) δ4.46-4.49 (0.6H, m), 4.37-4.41 (0.4H, m), 3.68 (1.2H, s), 3.66 (1.8H, s), 2.65-2.78 (1H, m), 2.14-2.23 (0.6H, m), 1.98-2.04 (0.4H, m), 1.84-1.94 (1H, m), 1.65-1.80 (3H, m), 1.52-1.61 (1H, m), 0.87 (3.6H, s), 0.85 (5.4H, s), 0.04 (3.6H, s), 0.02 (2.4H, s).

Step C: 2-t-butyldimethylsiloxycyclopentanecarbaldehyde

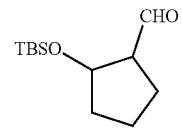 [SMILES: CC(C)(C)[Si](C)(C)OC1CCCC1C=O]

To a solution of racemic methyl 2-t-butyldimethylsiloxycyclopentanecarboxylate (20.0 g, 77.4 mmol) in n-hexane was added a 1.0 M solution of diisobutylaluminum hydride in toluene (80 mL, 80 mmol) dropwise at −78° C., and reacted for 1 hour. After completion of the reaction, 45 mL of methanol was added to quench the reaction. After removing a cold bath, the reaction solution was naturally warmed to room temperature. Then 800 mL of a Rochelle salt aqueous solution with a concentration of 10% was added, and vigorously stirred for 2 hours. The resulting solution was left to stand and layered. The n-hexane phase was collected, and the aqueous phase was extracted with n-hexane (500 mL×2). The organic phase was combined, washed with a saturated aqueous solution of sodium chloride (500 mL×2), and then dried over anhydrous sodium sulfate. The organic solvent was removed by distillation under reduced pressure to afford 2-t-butyldimethylsiloxycyclopentanecarbaldehyde as light yellow oily liquid (15.5 g, 87.6%).

$^1$H NMR (400 MHz, CDCl$_3$-d$_3$) δ9.76 (0.6H, d, J=2.4 Hz), 9.72 (0.4H, d, J=2.0 Hz), 4.63-4.66 (0.6H, m), 4.42-4.46 (0.4H, m), 2.63-2.79 (1H, m), 2.14-2.23 (0.6H, m), 1.56-2.04 (5.4H, m), 0.89 (5.4H, s), 0.87 (3.6H, s), 0.07 (3.6H, s), 0.06 (2.4H, s).

Step D: 3-[2-(t-butyldimethylsiloxy)cyclopentyl]acrylonitrile

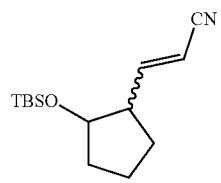 [SMILES: CC(C)(C)[Si](C)(C)OC1CCCC1C=CC#N]

2-T-butyldimethylsiloxycyclopentanecarbaldehyde (12.0 g, 52.5 mmol) and triphenylphosphine acetonitrile (31.6 g, 105 mmol) were dissolved in toluene (400 mL), heated to 110° C. under the protection of nitrogen gas, and reacted overnight (for 15 hours) at that temperature. After completion of the reaction, the reaction mixture was cooled to room temperature, and quenched by adding 800 mL of water. Then, the product was extracted with ethyl acetate (600 mL×2). The organic phase was combined, washed with a saturated aqueous solution of sodium chloride (700 mL×2), and then dried over anhydrous sodium sulfate. After the concentration under reduced pressure, the residue was slurried with petroleum ether to remove triphenylphosphine oxide. The filtrate was concentrated, and then separated by silica gel column chromatography (ethyl acetate:petroleum ether=50:1 as eluent) to afford 3-[2-(t-butyldimethylsiloxy)cyclopentyl]acrylonitrile (8.0 g, 60.6% yield).

$^1$H NMR (400 MHz, CDCl$_3$-d$_3$) δ6.82 (0.4H, dd, J=16.8 Hz, 8.4 Hz), 6.58-6.65 (0.6H, m), 5.29-5.36 (1H, m), 4.19-4.26 (1H, m), 2.87-2.95 (0.4H, m), 2.44-2.52 (0.6H, m), 1.57-1.94 (6H, m), 0.88 (3.6H, s), 0.87 (5.4H, s), 0.04 (2.4H, s), 0.03 (3.6H, s).

Step E: 3-(2-hydroxylcyclopentyl)acrylonitrile

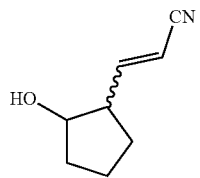

3-[2-(t-butyldimethylsiloxy)cyclopentyl]acrylonitrile (4.0 g, 15.9 mmol) was dissolved in a mixed solvent of anhydrous methanol (40 mL), 12.2 M hydrochloric acid (12 mL), and water (15 mL), and stirred for 0.5 hour at room temperature. After completion of the reaction, 80 mL of water was added, and the aqueous phase was extracted with ethyl acetate (100 mL×2). The organic phase was combined, washed with a saturated aqueous solution of sodium chloride (100 mL×2), and then dried over anhydrous sodium sulfate. The organic solvent was removed by distillation under reduced pressure, and the residue was separated by silica gel column chromatography to afford 3-(2-hydroxylcyclopentyl)acrylonitrile as light yellow oily liquid (2.18 g, 100%).

$^1$H NMR (400 MHz, CDCl$_3$-d$_3$) δ6.74 (1H, dd, J=11.2 Hz, 10.0 Hz), 5.40 (1H, d, J=11.2 Hz), 4.34-4.36 (1H, m), 2.94-3.00 (1H, m), 1.90-2.04 (3H, m), 1.69-1.78 (3H, m), 1.28-1.44 (1H, brs).

Step F: 3-[3-amino-4-(7-{[2-(trimethyl silyl)ethoxy]methyl}-7H-pyrrolo[2,3-d]pyrimidin-4-yl)-1H-pyrazol-1-yl]-3-(2-hydroxylcyclopentyl)propionitrile

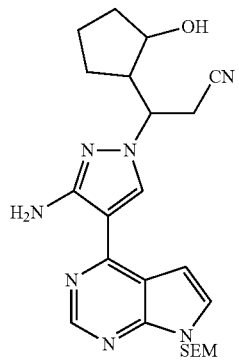 [SMILES: C[Si](C)(C)CCOCn1ccc2c(-c3cn(C(CC#N)C4CCCC4O)nc3N)ncnc21]

3-(2-Hydroxylcyclopentyl)acrylonitrile (1.4 g, 10.2 mmol), 4-(7-{[2-(trimethylsilyl) ethoxy]methyl}-7H-pyrrolo[2,3-d]pyrimidin-4-yl)-3-amino-1H-pyrazole (2.2 g, 6.8 mmol), and DBU (2.1 g, 13.6 mmol) were dissolved in 30 mL of acetonitrile, and stirred overnight (for about 15 hours) at 70° C. After the reaction mixture was cooled to room temperature, 60 mL of water was added thereto, and the resulting solution was extracted with ethyl acetate (60 mL×3). The organic phase was combined, washed with a saturated sodium chloride solution (100 mL×2), and then dried over anhydrous sodium sulfate. The organic solvent was removed by distillation under reduced pressure, and the residue was separated by silica gel column chromatography (a mixed solvent of dichloromethane:methanol=100:1 as an eluent) to afford 3-[3-amino-4-(7-{[2-(trimethylsilyl)ethoxy]methyl}-7H-pyrrolo[2,3-d]pyrimidin-4-yl)-1H-pyrazol-1-yl]-3-(2-hydroxylcyclopentyl)propionitrile as a diastereoisomeric mixture (1.3 g, 40% yield). The mixture was separated by silica gel thin layer chromatography (dichloromethane:methanol=30:1) to afford three isomers, which were A1, A2, and A3, respectively.

Isomer A1: $^1$H NMR (400 MHz, CDCl$_3$-d$_3$) δ8.80 (1H, s), 8.15 (1H, s), 7.34 (1H, d, J=3.6 Hz), 6.68 (1H, d, J=3.6 Hz), 5.56-5.96 (2H, brs), 5.66 (2H, s), 4.54-4.59 (1H, m), 3.87-3.93 (1H, m), 3.53 (2H, t, J=8.0 Hz), 3.11 (1H, dd, J=16.8 Hz, 8.4 Hz), 2.92 (1H, dd, J=16.8 Hz, 2.4 Hz), 2.32-2.45 (1H, m), 1.90-2.02 (1H, m), 1.54-1.87 (6H, m), 0.91 (2H, t, J=8.4 Hz), −0.06 (9H, s). m/z=468[M+1]$^+$.

Isomer A2: $^1$H NMR (400 MHz, CDCl$_3$-d$_3$) δ8.80 (1H, s), 8.15 (1H, s), 7.35 (1H, d, J=3.6 Hz), 6.70 (1H, d, J=3.6 Hz), 5.58-5.99 (2H, brs), 5.66 (2H, s), 4.13-4.18 (1H, m), 4.00-4.05 (1H, m), 3.53 (2H, t, J=8.4 Hz), 3.01 (1H, dd, J=16.8 Hz, 8.4 Hz), 2.90 (1H, dd, J=16.8 Hz, 3.6 Hz), 2.50-2.56 (1H, m), 2.07-2.14 (1H, m), 1.79-1.92 (2H, m), 1.65-1.71 (2H, m), 1.28-1.33 (2H, m), 0.92 (2H, t, J=8.0 Hz), −0.06 (9H, s). m/z=468[M+1]$^+$.

Isomer A3: $^1$H NMR (400 MHz, CDCl$_3$-d$_3$) δ8.80 (1H, s), 8.05 (1H, s), 7.35 (1H, d, J=4.0 Hz), 6.68 (1H, d, J=4.0 Hz), 5.41-5.80 (2H, brs), 5.66 (2H, s), 4.28-4.38 (1H, m), 3.90-4.00 (1H, m), 3.53 (2H, t, J=8.4 Hz), 3.19 (1H, dd, J=16.8 Hz, 8.8 Hz), 3.10 (1H, dd, J=16.8 Hz, 4.0 Hz), 2.33-2.43 (1H, m), 2.05-2.13 (1H, m), 1.56-1.87 (4H, m), 1.31-1.42 (2H, m), 0.92 (2H, t, J=8.0 Hz), −0.06 (9H, s). m/z=468 [M+1]$^+$.

Step G: 3-[3-amino-4-(7H-pyrrolo[2,3-d]pyrimidin-4-yl)-1H-pyrazol-1-yl]-3-(2-hydroxylcyclopentyl)propionitrile

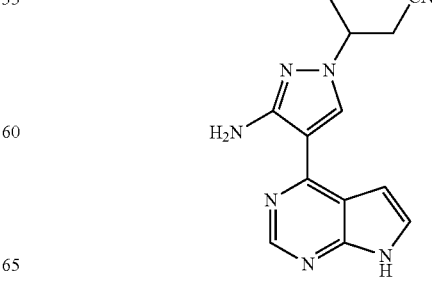

To a solution of each of three isomers A1, A2, and A3 of 3-[3-amino-4-(7-{[2-(trimethylsilyl)ethoxy]methyl}-7H-pyrrolo[2,3-d]pyrimidin-4-yl)-1H-pyrazol-1-yl]-3-(2-hydroxylcyclopentyl)propionitrile (13-57 mg, 1.0 eq.) in dichloromethane (5 mL) was added trifluoroacetic acid (0.5 mL) under stirring in an ice bath. Each of three reaction mixtures was stirred overnight under the protection of nitrogen gas at room temperature. After the reaction mixtures were concentrated in vacuo, the residues were dissolved in dichloromethane, and concentrated in vacuo twice. Each of three concentrates was dissolved in methanol (5 mL), and ethylenediamine (0.5 mL) was added thereto, stirred for 1 hour, and then concentrated in vacuo. Each of the resulting concentrates was diluted with water and ethyl acetate, and extracted with ethyl acetate. The combined organic phase was washed with a brine solution, dried over sodium sulfate, filtered, and concentrated in vacuo. The resulting three concentrates were separated by silica gel column chromatography, respectively, to afford three isomers 2a, 2b, and 2c of 3-[3-amino-4-(7H-pyrrolo[2,3-d]pyrimidin-4-yl)-1H-pyrazol-1-yl]-3-(2-hydroxylcyclopentyl)propionitrile (41%-69% yield).

Isomer 2a: $^1$H NMR (400 MHz, CDCl$_3$-d$_3$) δ9.24-9.30 (1H, brs), 8.80 (1H, s), 8.17 (1H, s), 7.32 (1H, d, J=2.4 Hz), 6.68 (1H, d, J=2.4 Hz), 5.64-5.81 (2H, brs), 4.55-4.61 (1H, m), 3.94 (1H, t, J=4.4 Hz), 3.13 (1H, dd, J=16.8 Hz, 8.8 Hz), 2.94 (1H, dd, J=16.8 Hz, 3.6 Hz), 2.37-2.46 (1H, m), 1.94-2.05 (1H, m), 1.54-1.88 (6H, m). m/z=338[M+1]$^+$.

Isomer 2b: $^1$H NMR (400 MHz, CDCl$_3$-d$_3$) δ9.77-9.88 (1H, brs), 8.77 (1H, s), 8.14 (1H, s), 7.29-7.30 (1H, m), 6.63 (1H, d, J=2.4 Hz), 6.45-5.90 (2H, brs), 4.11-4.20 (1H, m), 4.02-4.09 (1H, m), 3.03 (1H, dd, J=16.8 Hz, 8.8 Hz), 2.90 (1H, dd, J=16.8 Hz, 3.6 Hz), 2.51-2.59 (1H, m), 2.08-2.15 (1H, m), 1.79-1.99 (2H, m), 1.57-1.73 (4H, m). m/z=338 [M+1]$^+$.

Isomer 2c: $^1$H NMR (400 MHz, CDCl$_3$-d$_3$) δ9.25-9.30 (1H, brs), 8.84 (1H, s), 8.09 (1H, s), 7.36-7.38 (1H, m), 6.71-6.73 (1H, m), 5.68-5.88 (2H, brs), 4.33-4.38 (1H, m), 4.01-4.06 (1H, m), 3.24 (1H, dd, J=16.8 Hz, 9.2 Hz), 3.15 (1H, dd, J=16.8 Hz, 4.0 Hz), 2.40-2.49 (1H, m), 2.13-2.20 (1H, m), 1.86-1.97 (1H, m), 1.65-1.82 (4H, m), 1.44-1.51 (1H, m). m/z=338[M+1]$^+$.

Example 3 3-[3-amino-4-(7H-pyrrolo[2,3-d]pyrimidin-4-yl)-1H-pyrazol-1-yl]-3-(3-oxo cyclopentyl)propionitrile

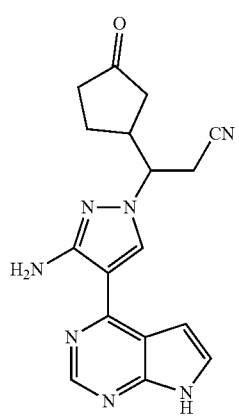 [SMILES: N#CCC(C1CCC(=O)C1)n1cc(-c2ncnc3[nH]ccc23)c(N)n1]

3-[3-amino-4-(7H-pyrrolo[2,3-d]pyrimidin-4-yl)-1H-pyrazol-1-yl]-3-(3-hydroxy 1 cyclopentyl)propionitrile (38 mg, 0.11 mmol) was dissolved in 10 mL of dry dichloromethane, and active manganese dioxide (294 mg, 3.38 mmol) was added under stirring at room temperature. The reaction solution was refluxed for 3 days under stirring. The resulting solution was cooled to room temperature, filtered through Celite, and concentrated under reduced pressure. The resulting concentrate was separated by silica gel thin layer chromatography (dichloromethane:methanol=15:1) to afford 3-[3-amino-4-(7H-pyrrolo[2,3-d]pyrimidin-4-yl)-1H-pyrazol-1-yl]-3-(3-oxocyclopentyl)propionitrile (13 mg, 34% yield).

$^1$H NMR (400 MHz, CD$_3$OD-d$_4$) δ8.67 (0.6H, s), 8.66 (0.4H, s), 8.50 (0.6H, s), 8.47 (0.4H, s), 7.42-7.43 (1H, m), 6.88 (0.6H, d, J=3.6 Hz), 6.87 (0.4H, d, J=3.6 Hz), 4.41-4.50 (1H, m), 3.03-3.24 (2H, m), 2.76-2.97 (1H, m), 2.47-2.54 (0.6H, m), 2.05-2.32 (3.4H, m), 1.62-1.85 (2H, m). m/z=336 [M+1]$^+$.

Example 4 3-[3-amino-4-(7H-pyrrolo[2,3-d]pyrimidin-4-yl)-1H-pyrazol-1-yl]-3-(2-oxocyclopentyl)propionitrile

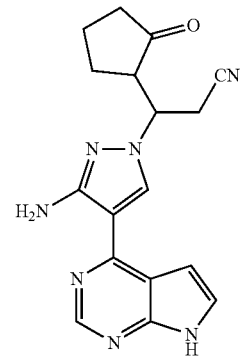 [SMILES: N#CCC(C1CCCC1=O)n1cc(-c2ncnc3[nH]ccc23)c(N)n1]

Step A: 3-[3-amino-4-(7-{[2-(trimethylsilyl)ethoxy]methyl}-7H-pyrrolo[2,3-d]pyrimidin-4-yl)-1H-pyrazol-1-yl]-3-(2-oxocyclopentyl)propionitrile

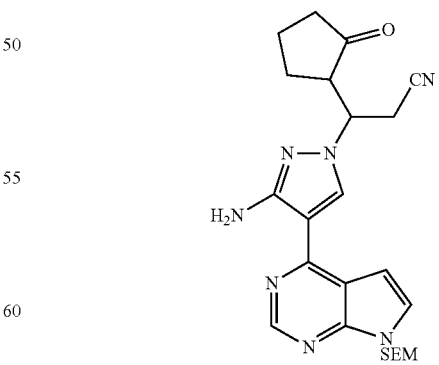

3-[3-amino-4-(7-{[2-(trimethylsilyl)ethoxy]methyl}-7H-pyrrolo[2,3-d]pyrimidin-4-yl)-1H-pyrazol-1-yl]-3-(2-hydroxylcyclopentyl)propionitrile (328 mg, 0.701 mmol) was dissolved in 50 mL of dry dichloromethane, and active manganese dioxide (2.1 g, 24 mmol) was added under stirring at room temperature. The reaction solution was refluxed for 5 days under stirring. The resulting solution was cooled to room temperature, filtered through Celite, and concentrated under reduced pressure. The resulting concentrate was separated by silica gel thin layer chromatography (dichloromethane:methanol=30:1) to afford 3-[3-amino-4-(7-{[2-(trimethylsilyl)ethoxy]methyl}-7H-pyrrolo[2,3-d]pyrimidin-4-yl)-1H-pyrazol-1-yl]-3-(2-oxo cyclopentyl) propionitrile (50 mg, 15% yield).

$^1$H NMR (400 MHz, CDCl$_3$-d$_3$) δ8.79 (1H, s), 8.02 (0.5H, s), 7.97 (0.5H, s), 7.33-7.39 (1H, m), 6.65-6.69 (1H, m), 5.58-6.01 (2H, brs), 5.66 (2H, s), 4.59-4.67 (0.5H, m), 4.45-4.55 (0.5H, m), 3.53 (2H, t, J=8.0 Hz), 3.43 (0.5H, dd, J=16.8 Hz, 4.8 Hz), 3.33 (0.5H, dd, J=16.8 Hz, 9.2 Hz), 3.21 (0.5H, dd, J=16.8 Hz, 9.2 Hz), 3.11 (0.5H, dd, J=16.8 Hz, 5.6 Hz), 2.63-2.78 (1H, m), 2.27-2.44 (2H, m), 1.90-2.17 (2H, m), 1.63-1.81 (2H, m), 0.92 (2H, t, J=8.0 Hz), −0.06 (9H, s). m/z=466[M+1]$^+$.

Step B: 3-[3-amino-4-(7H-pyrrolo[2,3-d]pyrimidin-4-yl]-1H-pyrazol-1-yl]-3-(2-oxocyclopentyl)propionitrile

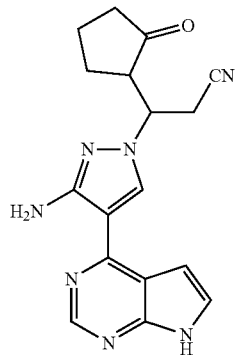 [SMILES: N#CCC(C1CCCC1=O)n1cc(-c2ncnc3[nH]ccc23)c(N)n1]

To a solution of 3-[3-amino-4-(7-{[2-(trimethylsilyl)ethoxy]methyl}-7H-pyrrolo[2,3-d]pyrimidin-4-yl)-1H-pyrazol-1-yl]-3-(2-oxocyclopentyl)propionitrile (50 mg, 0.107 mmol) in dichloromethane (5 mL) was added trifluoroacetic acid (1 mL) under stirring in an ice bath. The reaction solution was stirred overnight under the protection of nitrogen gas at room temperature. After the reaction solution was concentrated in vacuo, the residue was dissolved in dichloromethane, and concentrated in vacuo twice. The concentrate was dissolved in methanol (5 mL), and ethylenediamine (0.5 mL) was added, stirred for 0.5 hour at room temperature, and concentrated in vacuo. The resulting concentrate was diluted with water and ethyl acetate, and extracted with ethyl acetate. The combined organic phase was washed with a brine solution, dried over sodium sulfate, filtered, and concentrated in vacuo. The resulting concentrate was separated by silica gel thin layer chromatography to afford 3-[3-amino-4-(7H-pyrrolo[2,3-d]pyrimidin-4-yl)-1H-pyrazol-1-yl]-3-(2-oxocyclopentyl)propio nitrile (6 mg, 17% yield).

$^1$H NMR (400 MHz, CDCl$_3$-d$_3$) δ9.89-9.98 (1H, brs), 8.77 (1H, s), 8.03 (0.4H, s), 7.98 (0.6H, s), 7.30-7.36 (1H, m), 6.62-6.67 (1H, m), 5.55-5.90 (2H, brs), 4.62-4.68 (0.4H, m), 4.48-4.53 (0.6H, m), 3.11-3.49 (3H, m), 2.61-2.80 (1H, m), 2.27-2.45 (2H, m), 1.89-2.17 (2H, m), 1.63-1.82 (1H, m). m/z=336[M+1]$^+$.

Biological Activity Experiments

1. Assay for Enzymatic Activity (IC$_{50}$) of Compounds

A testing platform for kinase activity of JAK2 was established based on Homogeneous Time-Resolved Fluorescence (HTRF) assay, and the activities of the compounds were tested using the platform. The compounds were subjected to three-fold gradient dilutions with 100% DMSO with a starting concentration of 1 mM (11 dilutions in total). 4 μL of each dilution was added to 96 μL of reaction buffer (50 mM HEPES, pH 7.4, 10 mM MgCl$_2$, 1 mM EGTA, 0.01% Tween-20, 0.005% BAS, 2 mM DTT) and mixed homogeneously. 2.5 μL of the resulting liquid was then added to a 384-well plate (OptiPlate-384, available from PerkinElmer), and then 5 μL of JAK2 kinase (available from Cama) was added. The mixture was mixed homogeneously by centrifugation. Then 2.5 μL of a mixture of ATP (the final concentration is the corresponding K$_m$ value) and TK peptide (HTRF® KinEASE™-TK, available from Cisbio) was added to initiate the reaction (the total reaction volume is 10 μL). The 384-well plate was placed in an incubator and the reaction was allowed to conduct for 120 min at 23° C. Then the reaction was terminated by adding 5 μL of Eu3+ cryptate-labeled anti-phosphotyrosine antibody (available from Cisbio), and 5 μL of Streptavidin-XL-665 (HTRF® KinEASE™-TK, available from Cisbio). The plate was incubated in the incubator for 1 hr, and then the fluorescence values were read on Envision (available from PerkinElmer). The excitation wavelength was 320 nm, and the emission wavelengths for detection were 665 nm and 620 nm. The enzymatic activity was represented by a ratio of the two readout at the two emission wavelengths. The enzymatic activity for each compound was tested at 11 concentrations, and IC$_{50}$ values of the compounds were obtained by calculating the data using GraFit6.0 software (Erithacus Software)

The compounds prepared above were assayed according to the biological assays described herein, and the results thereof are shown below.

Inhibitory activity (IC$_{50}$) of compounds against JAK2 kinase

| Compound | JAK2 IC$_{50}$ (nM) |
| --- | --- |
| Ruxolitinib | <10 |
| Compound II | <10 |
| Compound III | <10 |
| Compound IV | <30 |

2. Plasma Protein Binding Assay and Human Liver Microsomal Stability Test of Compound Determination of Free Moiety:

Protein binding to the tested compounds was determined by equilibrium dialysis using a Rapid Equilibrium Dialysis (RED) Device system. The dialysis was performed for 5 hours in human plasma at 37° C. The compound II, the compound III, and the compound IV were incubated at 10 μM, and the compound I was incubated at 1 μM and 10 μM. The concentrations of the compounds in plasma and a buffer solution after dialysis were determined through LC-MS/MS analysis. The free moiety is defined as a ratio of the concentration in the buffer solution to the concentration in the plasma.

Determination of an Inherent Clearance:

1 μM of the tested compound was incubated for 1 hour together with human liver microsomes of mixed genders (0.4 mg/mL protein) in the presence of 1.25 mM NADPH at 37° C. to determine the inherent clearance. The disappearance of the tested compound was monitored by LC-MS/MS at 0, 10, 20, 30, 45, and 60 minute. By using the standard method reported in literatures, the declination slope of the concentration of the compound was used to calculate the inherent clearance of human.

TABLE 3

Results of Plasma Protein Binding Assay and Human Liver Microsomal Stability Test of Compound

| Compound | Unbound moiety (% human plasma) | Human liver microsome $T_{1/2}$ (h) | Human inherent CL (L/h/kg) |
|---|---|---|---|
| Compound I[a] | 4.3 | 2.76 | 0.45 |
| Compound II | 28.8 | >4 | <0.31 |
| Compound III | 30.4 | >4 | <0.31 |
| Compound IV | 24.3 | >4 | <0.31 |

Note
[a]Compound I is (3R)-3-[3-amino-4-(7H-pyrrolo[2,3-d]pyrimidin-4-yl)-1H-pyrazol-1-yl]-3-cyclopentylpropionitrile As shown in Table 3, in the human plasma protein binding assay, the compound II, the compound III, and the compound IV have higher free moieties than the compound I; and in human liver microsome, the compound II, the compound III, and the compound IV have higher stability, longer half life ($T_{1/2}$), and lower plasma clearance (CL) than the compound I.

What is claimed is:

1. A compound represented by formula A, a stereoisomer thereof, or a pharmaceutically acceptable salt thereof:

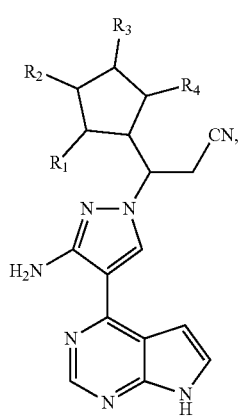

A wherein $R_1$ and $R_4$ are each independently selected from the group consisting of H, hydroxyl, and oxo; and $R_2$ and $R_3$ are each independently selected from the group consisting of H, and oxo; with the proviso that $R_1$, $R_2$, $R_3$, and $R_4$ are not all H.

2. The compound represented by formula A according to claim 1, wherein $R_1$ and $R_2$ are both H.

3. The compound represented by formula A according to claim 1, wherein one of $R_3$ and $R_4$ is H, and the other is hydroxyl or oxo.

4. The compound according to claim 1, wherein the compound is selected from the group consisting of:

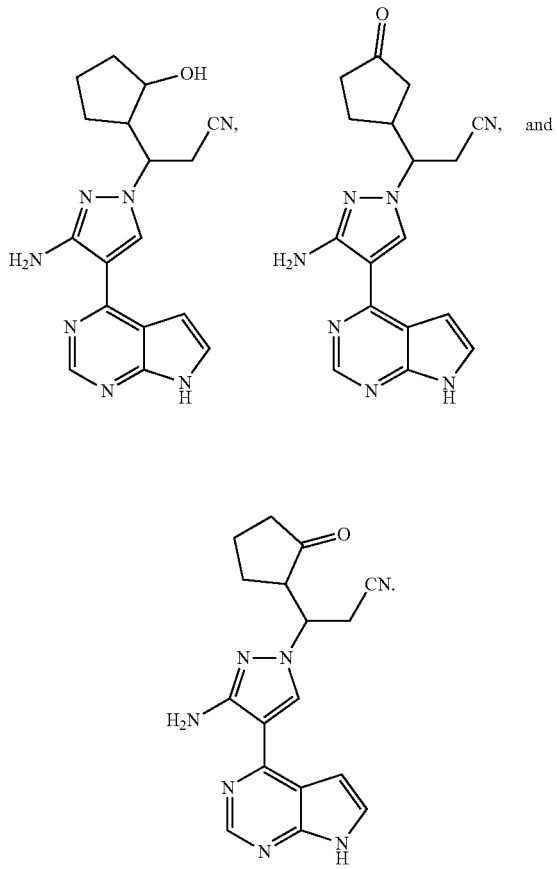

5. A pharmaceutical composition, comprising the compound according to claim 1, a stereoisomer thereof, or a pharmaceutically acceptable salt thereof, and one or more pharmaceutically acceptable carriers or excipients.

6. A pharmaceutical composition, comprising the compound according to claim 4, a stereoisomer thereof, or a pharmaceutically acceptable salt thereof, and one or more pharmaceutically acceptable carriers or excipients.

7. A method for treating a disease mediated by Janus kinase, comprising administering to a patient a therapeutically effective amount of the compound according to claim 1, a stereoisomer thereof, or a pharmaceutically acceptable salt thereof, wherein the disease mediated by Janus kinase is lymphoma or leukemia.

8. The method according to claim 7, further comprising administering to a patient one or more pharmaceutically acceptable carriers or excipients.

9. A method according to claim 7, wherein the compound is selected from the group consisting of:

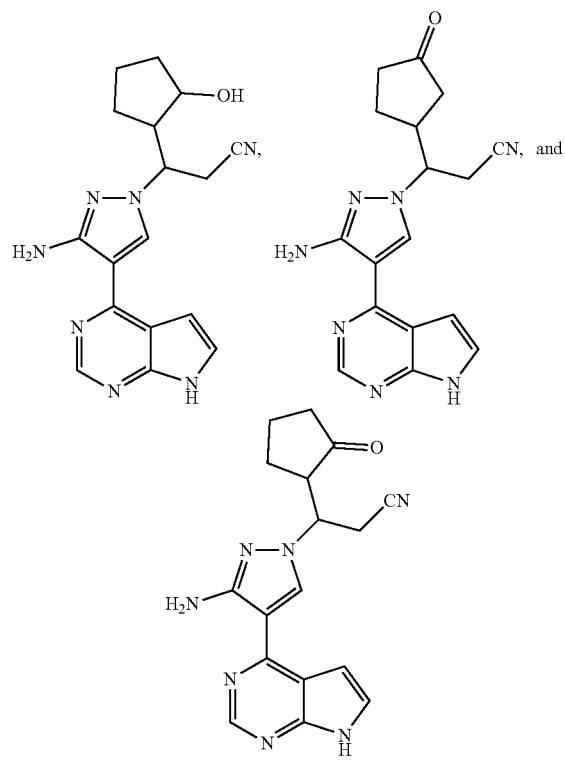

or a stereoisomer thereof, or a pharmaceutically acceptable salt thereof.

10. The method according to claim 9, further comprising administering one or more pharmaceutically acceptable carriers or excipients.

11. A method for inhibiting Janus kinase, comprising administering an effective amount of the compound according to claim 1.

12. The method according to claim 11, further comprising administering one or more pharmaceutically acceptable carriers or excipients.

13. The method according to claim 11, wherein the compound is selected from the group consisting of:

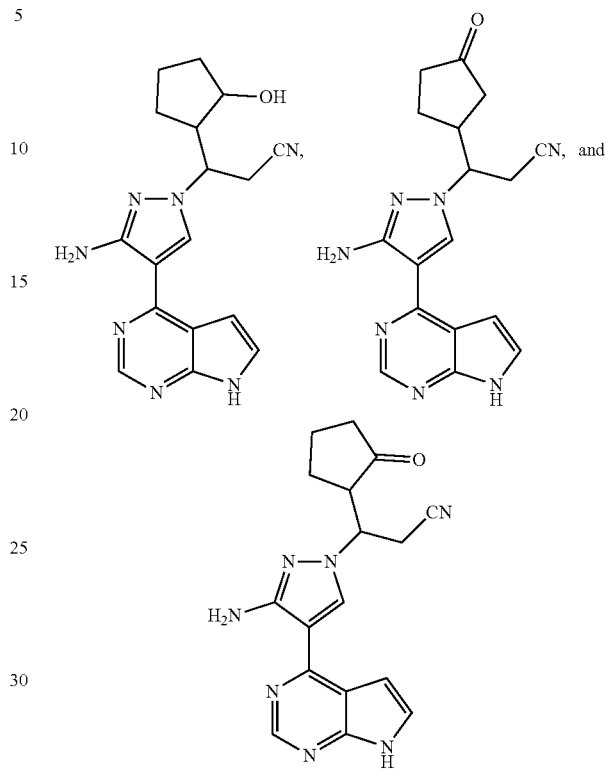

or a stereoisomer thereof, or a pharmaceutically acceptable salt thereof.

14. The method of claim 13, further comprising administering one or more pharmaceutically acceptable carriers or excipients.

* * * * *